(12) United States Patent
Brookler

(10) Patent No.: US 7,781,419 B2
(45) Date of Patent: *Aug. 24, 2010

(54) USE OF BISPHOSPHONATES FOR OTOSCLEROSIS

(76) Inventor: Kenneth H. Brookler, 119 Gregory Blvd., Unit 49, Norwalk, CT (US) 06855

( * ) Notice: Subject to any disclaimer, the term of this patent is extended or adjusted under 35 U.S.C. 154(b) by 0 days.

This patent is subject to a terminal disclaimer.

(21) Appl. No.: 12/371,184

(22) Filed: Feb. 13, 2009

(65) Prior Publication Data

US 2009/0181108 A1 Jul. 16, 2009

Related U.S. Application Data

(62) Division of application No. 10/926,565, filed on Aug. 25, 2004, now Pat. No. 7,511,028.

(60) Provisional application No. 60/499,155, filed on Aug. 29, 2003.

(51) Int. Cl.
*A61K 31/675* (2006.01)
*A61K 31/66* (2006.01)
*A61K 31/59* (2006.01)
(52) U.S. Cl. .......................... 514/89; 514/102; 514/167
(58) Field of Classification Search .................. 514/89, 514/102, 167
See application file for complete search history.

(56) References Cited

U.S. PATENT DOCUMENTS

| 5,994,329 | A | 11/1999 | Daifotis et al. |
| 6,008,206 | A | 12/1999 | Dohi et al. |
| 7,511,028 | B2 * | 3/2009 | Brookler ...................... 514/89 |
| 2001/0044427 | A1 | 11/2001 | Mazel et al. |

FOREIGN PATENT DOCUMENTS

SU 1410983 7/1988

OTHER PUBLICATIONS

Abramowicz et al., "Drugs For Prevention And Treatment Of Postmenopausal Osteoporosis," The Medical Letter On Drugs and Therapeutics, Oct. 16, 2000, 42(1009):97-100.
Abramowicz et al., "Tiludronate for Paget's Disease of Bone," The Medical Letter On Drugs and Therapeutics, Jul. 18, 1997, 39(1005):65-68.
Actonel label, approved by the FDA in May 2002.
Allen et al., "Calcinosis And Metastatic Calcification due to Vitamin D Intoxication," Horm. Res., 1992, 37:68-77.
Boumans et al., "The detrimental effect of aminohydroxypropylidene bisphosphonate (APD) in otospongiosis," Eur Arch Otorhinolaryngol. 1991;248(4):218-21.
Brookler et al., 1997, "Etidronate for the Neurotologic Symptoms of Otosclerosis:Preliminary Study," ENT Journal., vol. 76, No. 6.
Brookler, 2005, "Letter to the Editor: Questioning the relationship between cochlear otosclerosis and sensorineural hearing loss," Laryngoscope, vol. 115, No. 4: p. 757.
Brookler, K. H. et al., "Recurrent dizziness with abnormal findings on only one ENG test—the simultaneous binaural bithermal." Ear Nose and Throat Journal, vol. 81, No. 9, pp. 616-617, (2002).
Chole et al., "Basic Science Review Pathophysiology of Otosclerosis." Otology & Neurotology, vol. 22 pp. 249-257 (2001).
Columbia-Presbyterian Medical Center, "Expanded Clinic Targets Osteoporosis."•P&S Journal (1996), vol. 16 No. 3.
D. G. Little et al., "Intravenous pamidronate reduces osteoporosis and improves formation of the regenerate during distraction osteogenesis."•The Journal of Bone and Joint Surgery, vol. 83-8, No. 7, (2001).
Delmas et al., "Effects of raloxifene on bone mineral density, serum cholesterol concentrations, and uterine endometrium in postmenopausal women," N. Engl. J. Med., Dec. 4, 1997;337(23):1641-7.
Erik G. Nelson et al., "Questioning the Relationship between Cochlear Otosclerosis and Sensorineural Hearing Loss: A Quantitative Evaluation of Cochlear Structures in Cases of Otosclerosis and Review of the Literature." The Laryngoscope vol. 114, Jul. 2004.
Ettinger et al., "Reduction of vertebral fracture risk in postmenopausal women with osteoporosis treated with raloxifene: results from a 3-year randomized clinical trial. Multiple Outcomes of Raloxifene Evaluation (MORE) Investigators," JAMA. Aug. 18, 1999;282(7):637-45.
Gennari et al., "Diphosphonate Therapy in Deafness Associated With Paget's Disease," British Medical Journal, Feb. 8, 1975, p. 331.
Harris et al., "Effects of risedronate treatment on vertebral and nonvertebral fractures in women with postmenopausal osteoporosis: a randomized controlled trial. Vertebral Efficacy With Risedronate Therapy (VERT) Study Group," JAMA. Oct. 13, 1999;282(14):1344-52.
Head, 1999, "Ipriflavone: an important bone-building isoflavone." Altern Med Rev. 4(1):10-22.
Heaney et al., "Risedronate Reduces the Risk of First Vertebral Fracture in Osteoporotic Women," Osteoporos Int., 2002;13(6):501-5.
Hosking et al., "Prevention of bone loss with alendronate in postmenopausal women under 60 years of age. Early Postmenopausal Intervention Cohort Study Group," N. Engl. J. Med. Feb. 19, 1998;338(8):485-92.
Kennedy et al., "The effects of etidronate disodium on progressive hearing loss from otosclerosis," Otolaryngol Head Neck Surg. Sep. 1993;109(3 Pt 1):461-7.

(Continued)

*Primary Examiner*—Raymond J Henley, III
(74) *Attorney, Agent, or Firm*—Baker Botts L.L.P.

(57) ABSTRACT

A method of treating otosclerosis in a human in need thereof by administering a bisphosphonate in a defined dosing schedule. The invention demonstrates an effective response and sustained benefit in the treatment of otosclerosis. Particularly, the method involves administration of a bisphosphonate in a stepped-up dosage amount, e.g., in a dose that is at least one and a half times the recommended dose for osteoporosis. It also includes administration of a time-dependent dose of more than one bisphosphonate, specifically, alternating administration of a first bisphosphonate with a second bisphosphonate. The inventive method further includes intravenous administration of a bisphosphonate, and optionally oral administration of a bisphosphonate. The present invention further contemplates a kit for facilitating the alternating bisphosphonate dosing schedule.

21 Claims, No Drawings

OTHER PUBLICATIONS

Khetarpal et al., "In Search Of Pathologic Correlates For Hearing Loss And Vertigo In Paget's Disease: A Clinical And Histopathologic Study Of 26 Temporal Bones," Ann. Otol. Rhinol. Laryngol Suppl., Mar. 1990;145:1-16.

Lando et al., "Stabilization Of Hearing Loss In Paget's Disease With Calcitonin And Etidronate," Arch. Otolargynol Head Neck Surg., Aug. 1998, 114:891-894.

Levinson et al., "Primary prevention of postmenopausal osteoporosis," JAMA. Dec. 2, 1998;280(21):1821-2.

McClung et al., "Effect of risedronate on the risk of hip fracture in elderly women. Hip Intervention Program Study Group," N. Engl. J. Med. Feb. 1, 2001;344(5):333-40.

Meunier et al., "Paget's Disease of Bone: Clinicial Assessment, Present And Future Therapy," Proceedings of the Symposium On the Treatment of Paget's Disease of Bone, Oct. 20, 1989, pp. 86-99.

NIH Consensus Development Panel on Osteoporosis Prevention, Diagnosis, and Therapy, Osteoporosis prevention, diagnosis, and therapy, JAMA. Feb. 14, 2001;285(6):785-95.

Ohnishi, H. et al., "Bisphosphonate Tiludronate Increases Bone Strength by Improving Mass and Structure in Established Osteopenia After Ovariectomy in Rats." Bone vol. 21, No. 4, pp. 335-343 (1997).

Reid et al., 1995, "Ototoxicity associated with intravenous bisphosphonate administration," Calcif. Tissue Int., vol. 56, No. 6: p. 584-585.

Richardson et al., "Risedronate activity in the fetal and neonatal mouse," Otolaryngol Head Neck Surg. Oct. 1993;109(4):623-33.

Russell et al., 2007, "Bisphosphonates: an update on mechanisms of action and how these relate to clinical efficacy." Ann NY Acad Sci. 1117:209-57.

Singer et al., "Risedronate, a highly effective oral agent in the treatment of patients with severe Paget's disease," J. Clin. Endocrinol Metab. Jun. 1998;83(6):1906-10.

Stutzmann et al., "Diphosphonates For Otospongiosis," The American Journal Of Otology, Jan. 1985, 6(1):89-95.

Sziklai et al., 1992/93, "Double-blind study on the effectiveness of a bioflavonoid in the control of tinnitus in otosclerosis." Acta Chir Hung. 33(1-2):101-7.

Watts, 1998, "Treatment of osteoporosis with bisphosphonates," Endocrinol. Metab. Clin. North Am., vol. 27, No. 2: p. 419-439.

Watts, 2003 "Bisphosphonate treatment of osteoporosis," Clin. Geriatr. Med., vol. 19, No. 2:p. 395-414.

Yesil et al., "Further hearing loss during osteoporosis treatment with etidronate," Postgrad Med J. Jun. 1998;74(872):363-4.

Zehnder et al., "Osteoprotegrin knockout mice demonstrate abnormal remodeling of the otic capsule and progressive hearing loss," Laryngoscope. Feb. 2006;116(2):201-6.

Zizic et al., "The Use of Risedronate to Reduce the Risk of First Vertebral Fracture:Implications for Osteoporotic Women," JournalPlus, Feb. 2003.

U.S. Appl. No. 10/926,565, filed Aug. 25, 2004.

U.S. Appl. No. 10/926,565, Oct. 25, 2006 Non-Final Office Action.

U.S. Appl. No. 10/926,565, Jan. 25, 2007 Response to Non-Final Office Action.

U.S. Appl. No. 10/926,565, Jan. 15, 2008 Final Office Action.

U.S. Appl. No. 10/926,565, Apr. 9, 2008 Response to Final Office Action.

U.S. Appl. No. 10/926,565, May 6, 2008 Final Office Action.

U.S. Appl. No. 10/926,565, Oct. 23, 2008 Response to Final Office Action.

U.S. Appl. No. 10/926,565, Nov. 18, 2008 Notice of Allowance.

* cited by examiner

USE OF BISPHOSPHONATES FOR OTOSCLEROSIS

PRIORITY CLAIMED

This application is a divisional application of U.S. patent application Ser. No. 10/926,565, filed Aug. 25, 2004, now U.S. Pat. No. 7,511,028, which claims priority under 35 U.S.C. §119 to U.S. Application Ser. No. 60/499,155, filed Aug. 29, 2003, the disclosures of which are hereby incorporated by reference in their entireties herein.

FIELD OF THE INVENTION

The present invention is directed to a method of treating otosclerosis in a human in need thereof with the administration of a bisphosphonate, particularly in a stepped-up dosage amount, e.g., in a dose that is at least one and a half times the recommended dose for osteoporosis. The present invention is also directed to a method of treating otosclerosis in a human in need thereof with the administration of a time-dependent dose of more than one bisphosphonate, specifically, alternating administration of a first bisphosphonate with a second bisphosphonate. The inventive method of treating otosclerosis in a human in need thereof also includes intravenous administration of a bisphosphonate, or intravenous administration with a dosing schedule of oral bisphosphonate administration. The present invention further contemplates a kit for ease of administration of the alternating bisphosphonate dosing schedule.

BACKGROUND OF THE INVENTION

Otosclerosis is a bony dyscrasia of the capsule of the bone around the inner ear. The first sign of otosclerosis is a small growth of spongy bone tissue around the inner ear. This softened bone interferes with the way the inner ear works, producing a broad range of unfavorable symptoms such as mechanical hearing loss, inner ear or sensorineural hearing loss, dizziness, tinnitus, and Meniere's syndrome. Mechanical hearing loss occurs when this overgrown soft bone interferes with the vibration of the last bone next to the inner ear, and can go on to a total hearing loss.

The diagnosis for otosclerosis remains difficult to make. It often requires special x-rays of the inner ears; thorough knowledge of the anatomy and pathology of the ear, especially as related to otosclerosis; patient clinical information including history, physical examination; and results of patient hearing and auditory tests.

Treatment for otosclerosis is equally difficult. There is no known medicine available for treating otosclerosis. In the 1960's the only treatment for this disorder was to supplement the diet with sodium fluoride. In 1969, patients were placed on sodium fluoride and calcium carbonate. However, only some patients receiving these treatments experienced an improvement in symptoms. A hearing aid may be worn; however, natural hearing is preferred, if possible. Currently, surgery (e.g., a stapedectomy) has been found to be the most effective method of managing the mechanical hearing loss of otosclerosis. A stapedectomy is removal of the stapes bone. However, a stapedectomy is not 100% effective, and there are risks and complications of the procedure. In some instances, surgery can worsen the hearing loss or result in no improvement in hearing or no change in tinnitus. Potential side effects of a stapedectomy include a change in sense of taste on the same side of the tongue, vertigo, perforation of the tympanic membrane, and intolerance of very loud noises. In addition, treatment of the symptoms of otosclerosis has involved dietary modifications, such as a diet of low salt, low sugar, and low in saturated fats.

In 1997, it was found that bisphosphonates could be useful in the treatment of otosclerosis. Bisphosphonates have been approved by the FDA for use in the treatment of Paget's disease of bone and for osteoporosis. Conventional dosage amounts, e.g., those approved by the FDA, or those recommended in scientific literature, result in some benefit for otosclerosis patients, although the effect could be limited and in some cases transient.

Thus, there exists a need in the art to treat the sensorineural hearing loss, dizziness, tinnitus, and Meniere's disease that occurs with otosclerosis, and a need to adapt new dosage therapies for treating otosclerosis, eliminating or delaying the need for surgical intervention and/or dietary modifications.

SUMMARY OF THE INVENTION

It has now been discovered in the present invention that administration of one or more bisphosphonates in a defined dosing schedules has an effective response and sustained benefit in the treatment of otosclerosis.

Accordingly, the invention provides a method of treating otosclerosis in a human in need thereof, comprising administration of a bisphosphonate in a stepped up dosing schedule, e.g., in a dose that is at least one and a half times the recommended dose for osteoporosis. Thus, for many bisphosphonates, the dosage administered comprises at least about 150% of the recommended dose for osteoporosis. Administration of the bisphosphonate may be in a single weekly dose, or administration may be periodic, e.g., administered in divided doses of two, three, four, five, six, or seven times weekly. Preferably, the bisphosphonate is administered at least one hour before eating or drinking (other than water) after an appropriate fasting period, e.g., upon awakening. The bisphosphonate is also preferably administered in an amount and at selected intervals, so as to achieve and sustain the desirable absorption of the drug into the bone.

The invention further provides a method of treating otosclerosis in a human in need thereof, comprising an alternating dosing schedule of two different bisphosphonates. In a specific embodiment, a first bisphosphonate is risedronate and a second bisphosphonate is etidronate, or pharmaceutically acceptable salts thereof.

In another alternating dosing schedule, a first bisphosphonate is etidronate and a second bisphosphonate is zolendronic acid, or pharmaceutically acceptable salts thereof.

In another embodiment, the method of treating otosclerosis comprises an alternating dosing schedule of two different bisphosphonates where each administered in a stepped up dosing schedule, e.g., in a dose that is at least about one and a half (150% of) the recommended dose for osteoporosis. Total weekly dosage of each of the two different bisphosphonates may be in a single weekly dose, or administration may be periodic, e.g., administered in divided doses of two, three, four, five, six, or seven times weekly. Preferably, the bisphosphonates are administered in a periodic dosing schedule at least one hour before eating and drinking (other than water) after an appropriate fasting period, e.g., upon awakening, so as to achieve an optimal effect as described above.

In yet another embodiment, the method of treating otosclerosis comprises an alternating dosing schedule of two different bisphosphonates, wherein a first bisphosphonate is administered in a stepped up dosing schedule, e.g., in a dose that is at least about one and a half (150%) of the recommended dose for osteoporosis and a second bisphosphonate is administered in a dosing schedule that is the recommended dose for osteoporosis.

The invention also provides a kit for administering the proper dosage in the alternate dosing schedule treatment. For example, blister packs with alternating dosages can be provided.

The invention further provides a method for prophylactic administration of a bisphosphonate to prevent the progression of otosclerosis in individuals with a family history of otosclerosis or those determined to be candidates for the disorder, but not yet diagnosed with otosclerosis.

The invention also provides for an intravenous dosing schedule of a bisphosphonate for patients unable to tolerate the oral dosing schedules or patients demonstrating no response to oral dosing schedules. In one embodiment, the intravenous dose is at least about one and a half times the recommended dose for osteoporosis. Preferably, intravenous administration is as needed and may be periodic, e.g., monthly, bimonthly, every 4 months, or every 6 months, so as to achieve an optimal effect. In another embodiment, the intravenous dosing schedule is administered in connection with a second bisphosphonate, such as etidronate.

For example, intravenous dosing includes, but is not limited to, the use of intravenous zolendronate, zolendronic acid, or ibandronate. Intravenous administration provides an efficient way of introducing medications to the bony structure of individuals in need thereof.

These and other aspects of the invention are discussed more in the detailed description and examples.

DETAILED DESCRIPTION OF THE INVENTION

The present invention advantageously provides a method of treatment of otosclerosis in a human in need thereof. According to the invention, the administration of a bisphosphonate in a novel dosing amount significantly lessens symptoms and has a sustained effect. The treatment appears to decrease or stop the progression of hearing loss, improve impaired hearing, lessen episodes of dizziness, and lessen symptoms associated with tinnitus and Meniere's disease.

The present invention is based upon the study of the treatment of patients with otosclerosis with the inventive dosing amount or schedule. In particular, patients taking a dose of the bisphosphonate risedronate on an FDA approved schedule prescribed for treating osteoporosis were instructed to take that dose twice per week. This resulted in an unexpected improvement in hearing, as reported in the Example 1. Example 2 is a follow up study of the treatment reported in Example 1. Patients taking a dose of the bisphosphonate risedronate on an FDA approved schedule prescribed for treating osteoporosis were instructed to take that dose twice per week. This resulted in an unexpected improvement e.g., hearing loss improved, decreased, or stayed the same; episodes of dizziness were lessened; and symptoms associated with tinnitus and Meniere's disease lessened. Example 3 is a study of administration of two different bisphosphonates. Example 4 is a study of intravenous bisphosphonate administration and intravenous bisphosphonate administration plus oral bisphosphonate administration.

The terms used in this specification generally have their ordinary meanings in the art, within the context of this invention and in the specific context where each term is used.

Certain terms are defined below to provide additional guidance in describing the compositions and methods of the invention.

The term Aabout@ or Aapproximately@ means within an acceptable error range for the particular value as determined by one of ordinary skill in the art, which will depend in part on how the value is measured or determined, i.e., the limitations of the measurement system or on the particular circumstances, i.e., the degree of precision required for a particular purpose, such as a pharmaceutical formulation. For example, Aabout@ can mean within 1 or more than 1 standard deviations, per the practice in the art. Alternatively, Aabout@ can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" means within an acceptable error range for the particular value.

As used herein, the terms "recommended dose for osteoporosis" or "recommended dosing schedule for osteoporosis" refer to any FDA approved dosing schedule, any dosing schedule approved by any other regulatory agency in the United States or abroad, any off-label prescribed dosing schedule for osteoporosis commonly known to those of ordinary skill in the art, or any preferred dosing schedule for osteoporosis appearing in scientific literature.

Bisphosphonate

As used herein "bisphosphonate" refers to a class of chemicals characterized by a nucleus designated P—C—P. These chemical formulations were initially used for the treatment of the disorder of bone called Paget's disease, for the treatment of hypercalcemia, for the treatment of osteoporosis, and for the prevention of postmenopausal osteoporosis. Examples of bisphosphonates, include but are not limited to, etidronate (1-hydroxyethyldiene diphosphonic acid) or the pharmaceutically acceptable salts thereof, such as, etidronate disodium; risedronate (pyridiniyl bisphosphonate) or the pharmaceutically acceptable salts thereof, such as, risedronate sodium; alendronate (4-amino-1-hydroxybutylidene) or the pharmaceutically acceptable salts thereof, such as, alendronate sodium; pamidronate (3-amino-1-hydroxypropylidene), or the pharmaceutically acceptable salts thereof, such as, pamidronate disodium; tiludronate [[[(4-chlorophenyl)thio]methylene]bis(phosphonic acid)] or the pharmaceutically acceptable salts thereof, such as, tiludrinate disodium; ibandronate or the pharmaceutically acceptable salts thereof, such as, ibandronate sodium; clondronate or the pharmaceutically acceptable salts thereof, and zolendronic acid.

Chemicals in this classification with an added amine have the ability to affect osteoclasts by reducing the rate of stimulation of osteoclasts. All chemicals in this classification have the ability to produce programmed cell death of osteoclasts.

The bisphosphonates are approved by the FDA for the treatment of Paget's disease, for the treatment of hypercalcemia, for the treatment of osteoporosis, and for the prevention of postmenopausal osteoporosis.

Several bisphosphonates and their recommended dosing schedules for osteoporosis appear in Table 1.

TABLE 1

Recommended Dosing Schedules for Osteoporosis

| | |
|---|---|
| Alendronate (Fosamax ®): | FDA approved dose: Postmenopausal osteoporosis prevention: 5 mg orally once daily or treatment: 10 mg orally once daily. Glucocorticoid induced: 5-10 mg orally once daily. Alendronate should be taken in the morning with 6 to 8 ounces of water at least one-half hour before food, beverages, or other medications. |
| Etidronate (Didronel ®): | Recommended by physicians and scientific literature: 400 mg per day × 2 weeks followed by a period of administration of a calcium supplement. Adami, S, et al., "Prevention of early postmenopausal bone loss with cyclical etidronate," Journal of Endocrinological Investigation 2000; 23(5): 310-316. |
| Pamidronate (Aredia ®): | Recommended by physicians and scientific literature: 30-90 mg IV single dose. Wait at least 7 days before considering retreatment. See Little, DG., "Intravenous pamidronate reduces osteoporosis and improves formation of the regenerate during distraction osteobenesis," Journal Bone & Joint Surgery 2001, Sept. 83(7): 1069-74, and FDA approved dose for hypercalcemia. |
| Risedronate (Actonel ®): | FDA approved dose: Osteoporosis prevention and treatment of: 5 mg orally once daily, 35 mg orally once weekly, or 30 mg orally once weekly. Should be taken on an empty stomach in an upright position with at least 6 ounces of plain water. The upright position and empty stomach should be maintained for at least 30 minutes to minimize gastrointestinal adverse events and increase absorption. |
| Tiludronate (Skelid ®): | Recommended by physicians and scientific literature: 400 mg orally once daily × 3 months. Each dose should be taken with 6 to 8 ounces of water. Tiludronate should not be taken within 2 hours of food or other medications. See Ohnishi H., et al., "Bisphosphonate tiludronate increases bone strength by improving mass and structure in established osteopenia ager ovariectomy in rats," Bone 1997 Oct. 21(4): 335-43 and FDA approved dose for Paget's disease. |
| Ibandronate (Boniva ®) | FDA approved dose: Osteoporosis prevention and treatment of: 2.5 mg orally once daily. A phase III study has investigated an intravenous injection in the amount of: 2 mg every two months and 3 mg every three months. |
| Zoledronic acid (Zometa ®) | Recommended dose: 4 mg zoledronic acid on an anhydrous basis. Note: FDA has not yet approved zoledronic acid for the treatment of osteoporosis. |

Otosclerosis

"Otosclerosis" as used herein refers to a bony dyscrasia of the capsule of the bone around the hearing and balance part of the inner ear. In the active phase there are seen to be abundant osteoclasts in the bone and a softening or spongiotic phase where it produces its most significant effect upon the inner ear. The sclerotic phase may still have elements of active demineralization of the bone around the inner ear, but also with a harder or sclerotic element to it. The recognizable clinical and less common form of otosclerosis occurs when there is an overgrowth of this bone where the last bone vibrates next to the inner ear and for which there is a surgical procedure. Is not possible simply by looking at this bone to decide whether it is spongiotic or sclerotic. However, to the naked eye it appears to be hard bone and therefore was called otosclerosis, although it may have been in its active phase and more aptly called otospongiosis. By common usage, both phases of this disorder are referred to as otosclerosis. Less recognizable, but more prevalent, are the disorders secondary to the effect of this softened bone around the inner ear. This can produce symptoms of progressive sensorineural hearing loss, tinnitus, dizziness, and when in a particular clinical combinations, Meniere's syndrome.

Diagnosis of Otosclerosis

The recognition of otosclerosis of the inner ear is difficult to perform. In some instances there is a family history of otosclerosis or of ear disorders in general or evidence on acoustic immittance of the middle ear findings of otosclerosis. In the absence of the foregoing, imaging of the area is one means of finding evidence of otosclerosis. Since the entire inner ear can be placed on a dime with plenty of room around it, the imaging modality must be able to produce a resolution sufficiently high enough to recognize the presence of this disorder.

Tinnitus

Tinnitus is a sensation of ringing, roaring, buzzing, or hissing in the ears or head. For many people, tinnitus is distracting and upsetting.

Meniere's Syndrome

Meniere's syndrome or disease is characterized by recurrent bouts of rotary feeling of dizziness with nausea and vomiting. Associated with the spells is hearing loss, usually in one ear, noise in that ear (tinnitus), and a feeling of fullness or a clogging. The spells from Meniere's syndrome may become more frequent or go on to chronic dizziness. The hearing loss may progress to a level that is not responsive to a hearing aid. The ear noise may remain constant and a distraction to the person suffering with the condition. The ear fullness may become constant and also a distraction. The conventional treatments include low salt diet, diuretics, and medicines to try to control the dizziness including tranquilizers. If these treatments do not work, then surgery may be tried to relieve the condition. In about 10 to 20% of people it may develop in the other ear.

Treatment of Otosclerosis

Stepped Up Dosing of Bisphosphonates

One embodiment of the present invention involves the treating of otosclerosis in a human in need thereof. This method involves administering a bisphosphonate at least one and a half times (150%) the recommended dose for osteoporosis, resulting in an unexpected improvement in hearing, as shown by improved range and sensitivity or cessation of further hearing loss, diminishment of tinnitus, and reduction in the symptoms of Meniere's syndrome beyond anything observed previously. In specific embodiments, the dosage of bisphosphonate administered comprises about 150% to 300% of the recommended dose for osteoporosis. The stepped-up dosing of bisphosphonates of the present invention is calculated herein as at least about 150% of the highest recommended dose for osteoporosis.

In a preferred embodiment, the bisphosphonate is risedronate. The risedronate administered is equal to a total of at least about 45 mg to 105 mg per week, preferably at least about 50 mg to 70 mg per week. In a specific embodiment, it is 60 mg per week. While this dosing schedule differs from the recommended treatment of osteoporosis, it appears most effective for otosclerosis.

Administration of the bisphosphonate may be in a single dose or divided. For example, if the bisphosphonate is risedronate, it may be in a single weekly dose or the total weekly dosage may be administered periodically in divided doses of two, three, four, five, six, or seven times weekly. Preferably, the bisphosphonate, e.g., risedronate, is administered at least one hour before eating and drinking (other than water) after an appropriate fasting period. The risedronate is also preferably administered in a dosage amount and at scheduled times so as to achieve optimal bone absorption and achieve an optimal effect. In another embodiment, the method of treating otosclerosis further includes administration of calcium and Vitamin D and/or calcium and fluoride.

In another preferred embodiment, the bisphosphonate is etidronate. The dosage of etidronate administered comprises at least 150% or preferably 150% to 300% of the recommended dose for osteoporosis. The etidronate administered is equal to a total of at least about 600 mg to 1200 mg per week for 1 to 3 weeks, every 6 to 13 weeks, preferably at least about 600 mg to 900 mg per week for 1 to 3 weeks, every 6 to 13 weeks. While this dosing schedule is not consistent with the recommended treatment of osteoporosis, it appears most effective for otosclerosis.

Administration of the etidronate may be in a single dose for the week in which it is administered or the total weekly dosage may be administered periodically in divided doses of from two to seven times weekly. Preferably, the etidronate is administered at least one hour before eating and drinking (other than water) after an appropriate fasting period. The etidronate is also preferably administered in a dosage amount and at scheduled times so as to achieve optimal bone absorption and achieve an optimal effect.

Additional embodiments of the stepped up dosing schedule are listed in Table 2. Each of the bisphosphonates listed are preferably administered once daily, in a single dose for the week, or the total weekly dosage may be administered periodically in divided doses of two to six times weekly. Preferably, the bisphosphonates are administered at least one hour before eating and drinking (other than water) after an appropriate fasting period. The bisphosphonates are also preferably administered in a dosage amount and at scheduled times so as to achieve optimal bone absorption and achieve an optimal effect.

TABLE 2

| Stepped up dosing schedule | |
|---|---|
| Alendrolate | 15 mg to 30 mg orally once daily. |
| Pamidronate | 135 mg to 270 mg IV single dose. |
| Tiludronate | 600 mg to 1200 mg orally once daily |
| Ibandronate | 3.75 mg to 7.5 mg orally once daily. |

Alternating Dosing of a First Bisphosphonate and a Second Bisphosphonate

In another embodiment, the present invention involves a method of treating otosclerosis in a human in need thereof, wherein the method comprises administration of two different bisphosphonates, e.g., a first bisphosphonate and a second bisphosphonate, in an alternating dosing schedule.

In one preferred embodiment, the first bisphosphonate is risedronate or a pharmaceutically acceptable salt thereof and the second bisphosphonate is etidronate or tiludronate or a pharmaceutically acceptable salts thereof.

In the alternate dosing schedule, (1) both of the bisphosphonates may be administered in accordance with a recommended dosing schedule for osteoporosis; (2) both of the bisphosphonates may be administered in a "stepped-up" dose, e.g., a dosing schedule that is at least 150% of the recommended dose for osteoporosis, or 150% to 300% of the recommended dose for osteoporosis; (3) the first bisphosphonate may be administered in accordance with the recommended dosing schedule for osteoporosis while the second bisphosphonate is administered in a dose that is at least 150% of the recommended dose for osteoporosis, or 150% to 300% of the recommended dose for osteoporosis; or (4) the second bisphosphonate may be administered in accordance with the recommended dosing schedule for osteoporosis while the first bisphosphonate is administered in a dose that is at least 150% of the recommended dose for osteoporosis or 150% to 300% of the recommended dose for osteoporosis.

In one embodiment of the alternate dosing schedule treatment, the administration of one bisphosphonate, risedronate, comprises a total of at least about 5 mg to 35 mg, preferably at least about 5 mg to 30 mg per week, for at least 1 to 52 weeks, preferably 2 to 26 weeks, followed by administration of the second bisphosphonate, such as etidronate, comprising a total of at least about 400 mg per week, for 1 to 3 weeks, every 6 to 13 weeks.

In another embodiment, the dosing schedule is at least 150%, or preferably 150% to 300%, of the recommended dose for osteoporosis. For example, the administration of the bisphosphonate, risedronate, comprises a total of at least about 45 mg to 105 mg per week, preferably at least about 50 mg to 70 mg per week, for at least 1 to 52 weeks, preferably 2 to 26 weeks, followed by administration of the second bisphosphonate, etidronate, comprising a total of at least about 600 mg to 1200 mg per week, preferably at least about 600 mg to 900 mg per week, for 1 to 3 weeks, every 6 to 13 weeks.

In a further embodiment, the administration of one bisphosphonate, risedronate, comprises a total of at least about 45 mg to 105 mg per week, preferably at least about 50 mg to 70 mg per week, for at least 1 to 52 weeks, preferably 2 to 26 weeks, followed by administration of the second bisphosphonate, etidronate, comprising a total of at least about 400 mg per week, for 1 to 3 weeks, every 6 to 13 weeks.

In another embodiment, the administration risedronate comprises a total of at least about 5 mg to 35 mg, preferably at least about 5 mg to 30 mg per week, for at least 1 to 52 weeks, preferably 2 to 26 weeks, followed by administration of etidronate comprising a total of at least about 600 mg to 900 mg per week, for 1 to 3 weeks, every 6-13 weeks.

Administration of each of the bisphosphonates may be in a single weekly dose, or the total weekly dosage may be administered periodically in divided doses of two, three, four, five, six, or seven times weekly. Preferably, the bisphosphonates are administered at least one hour before eating and drinking (other than water) after an appropriate fasting period. The bisphosphonates are also preferably administered in a dosage amount and scheduled time so as to achieve optimal bone absorption and achieve an optimal effect.

In a further embodiment, the alternate dosing schedule also includes continuous supplementation of calcium and Vitamin D and/or calcium and fluoride.

Intravenous Dosing of Bisphosphonates

In another embodiment, the present invention provides a method for treating otosclerosis in a human in need thereof, wherein the method comprises intravenous administration of a bisphosphonate in at least about 150% of the recommended dosage for osteoporosis or in the amount of an FDA approved dose for an indication other than osteoporosis, or in at least about 150% of the recommended dosage for an indication other than osteoporosis. In one preferred embodiment, the intravenously administered bisphosphonate is zolendronate. The intravenous treatment may also be supplemented with calcium, Vitamin D, or fluoride, or combinations thereof; or an orally administered bisphosphonate. An intravenous administration dosing schedule may be from about 2 mg to 6 mg, preferably from 3 mg to 5 mg, administered from about 2 to 10 times a year. Preferably, intravenous administration is in periodic dosage amounts as needed so as to achieve an optimal effect. Preferably, the supplemental treatment, e.g., with one or more of calcium, fluoride, Vitamin D, or combinations thereof; or an orally administered bisphosphonate is administered as needed. The supplemental orally administered bisphosphonate may be etidronate, risedronate, alendronate, or tiludronate.

Kits

One embodiment the present invention provides a kit for the administration of the alternating dosing schedule of two bisphosphonates as set forth above. For example, the kit can comprise a 1 to 52 week, preferably a 2 to 26 week, dose of one bisphosphonate, alternating with a 1 to 6 week dose, preferably a 2 to 4 week dose, of the second bisphosphonate. Instructions for administering the alternating dose may be included in the kit, or as part of the packaging of the kit.

Numerous kit formats are available. For example, a bubble pack, with unit doses of the bisphosphonates, can be provided. The bisphosphonates can be in pill, tablet, capsule, or other solid dosage form, with alternating or the same colors. Each dosage period can be arranged in rows or columns, or the doses can be arranged in a circle to be administered on the appropriate basis. In a circular pattern it may not be necessary to visually distinguish the two alternative bisphosphonates.

To ensure compliance with dosing, it may be advisable to provide a daily dose. In this case, if the optimal dosing regiment is less frequently than daily, identical placebos can be administered on the non-dosing days to maintain the regular doing pattern, and thus compliance.

Other kits, which may be appropriate for patients on many medications who arrange their medications on a weekly or other periodic schedule, may include two separate vials of oral dosage forms for the subject to arrange for the following week. Preferably such a kit also contains instructions.

EXAMPLES

To illustrate the advantages of the invention, patients with the following symptoms were treated.

Meniere's Syndrome

Patients were assessed for improvements in dizziness, i.e., disappearance of dizziness, or improvement in dizziness assessed as able to carry on a regular lifestyle free of disabling dizziness; hearing, i.e., better, same, or worse, where any cessation in the progression of hearing loss is a success; ear noise; and clogging or fullness in the ear.

Dizziness (with No Evidence of Meniere's Syndrome)

Patients were administered the bisphosphonate to see if dizziness could disappear or if associated symptoms of hearing loss or ear noise could be improved.

Hearing Loss

Hearing loss patients generally experience progressive loss of hearing. While the bisphosphonate treatment has resulted in some hearing gains, any cessation of the progression of the hearing loss is also a success.

Tinnitus

This symptom can be a mild distraction, to an annoyance, to difficulty concentrating, to a total distraction. The patients in this group had a primary presenting complaint of tinnitus bothering them to varying degrees. There are no current recognized treatments for tinnitus directed at a cause.

In all instances, prior to being administered the regimen of the invention, the patients had been on prior bisphosphonate treatment according to the recommended dose for osteoporosis.

Example 1

In the first study, the following populations having the symptom stated were treated with a dosing schedule of 30 mg risedronate twice weekly (double the recommended dose for treating osteoporosis). All patients received calcium plus vitamin D and/or calcium plus fluoride throughout the treatment.

TABLE 3

| Symptom | Patient Total | Male | Female | Age Range | Mean Age |
|---------|---------------|------|--------|-----------|----------|
| Meniere's syndrome | 36 | 19 | 17 | 22-80 | 53 |
| Dizziness | 76 | 22 | 54 | 23-88 | 55 |
| Hearing Loss | 46 | 19 | 27 | 39-80 | 60 |
| Tinnitus | 29 | 15 | 14 | 42-82 | 59 |

The following results were obtained:

Meniere's Syndrome after a Period of 2 to 25 Months

Eighteen patients (50%) saw their dizziness disappear, while 6 patients (16%) experienced an improvement such that they were able to carry on a regular lifestyle free of disabling dizziness. In no instances was the dizziness the same or worse with the inventive dosing schedule.

Thirty-three (83%) of the patients found their hearing to be better, while hearing was the same in three patients (8%), and hearing was worse than with the prior bisphosphonate treatment in three patients (8%). Ear noise cleared up in three patients (8%), was better in twenty-six (72%), and was unchanged in seven (19%). In no patient was it worse than before beginning on the inventive risedronate regimen. Clogging or fullness in the ear was not present in fifteen patients (42%), disappeared in six patients (17%), was better in eight patients (22%), and was the same in seven patients (19%). In no patient was it worse.

The results of this regimen are better than published surgical and other medical treatments for Meniere's syndrome.

Dizziness after a Period of 3 to 25 Months

Eleven patients (14%) had their dizziness disappear on previous bisphosphonate treatment and were given the stepped-up dose to see if associated symptoms of hearing loss or ear noise could be improved. Twenty-nine patients (38%) experienced disappearance of dizziness, and another 29 patients (38%) experienced reduced dizziness such that it represented no problem for them in daily living. Only five patients (8%) found no change in the dizziness and 2 patients (3%) found their dizziness worse than before the change to the twice weekly 30 mg risedronate. Remarkably, greater than 90% relief of dizziness was achieved with the stepped up dosing.

Hearing Loss after a Period of 3 to 24 Months

In 32 patients (70%) hearing improved, and in 11 patients (24%) hearing was unchanged. In 3 patients (6%) hearing was worse than when they embarked on the 30 mg twice-weekly dose of risedronate. Untreated, these patients would have been expected to undergo further decline in their hearing.

Tinnitus or Ear Noise after a Period of 3 to 19 Months

Two patients (7%) experienced disappearance of their tinnitus, while 18 patients (62%) experienced a reduction of tinnitus to a point where it was no longer a problem. In 7 patients (24%) it was the same as before the dose of 30 mg twice weekly and in 2 patients (7%) it was worse. Significantly, a 68% improvement in tinnitus or ear noise was achieved.

Example 2

In the second study, the following populations having the symptom stated were treated with a dosing schedule of 30 mg risedronate twice weekly (double the recommended dose for treating osteoporosis). All patients received calcium plus vitamin D and/or calcium plus fluoride throughout the treatment. The second investigation is cumulative to the first investigation, i.e., some patients reported in Example 1 are included in Example 2.

| Symptom | Patient Total | Male | Female | Age Range | Mean Age |
| --- | --- | --- | --- | --- | --- |
| Meniere's syndrome | 42 | 23 | 19 | 33-77 | 52 |
| Dizziness | 155 | 42 | 113 | 23-89 | 55 |
| Hearing Loss | 125 | 63 | 62 | 28-86 | 60 |
| Tinnitus | 84 | 42 | 42 | 29-84 | 58 |

The following results were obtained:

Meniere's Syndrome after a Period of 2 to 33 Months

Twenty-four patients (57%) of the entire group saw their dizziness disappear, while seven patients (17%) experienced an improvement such that they were able to carry on a regular lifestyle free of disabling dizziness. In no instances was the dizziness the same or worse with the stepped-up risedronate.

In addition, twenty-nine patients (69%) found their hearing to be better, while six patients (14%) found hearing was the same, and five patients (12%) reported hearing was worse than with the prior bisphosphonate treatment. Ear noise was gone in four (10%) of patients, better in twenty-five (60%) of patients, and the same in eight (19%) patients. Ear noise was worse in only one (2%) patient. Clogging or fullness in the ear disappeared in eleven (26%) of patients, better in eight (19%) of patients, and the same in three (7%) patients. In no patients was clogging or fullness in the ear worse.

The results of this regimen are better than published surgical and other medical treatments for Meniere's syndrome.

Dizziness after a Period of 2 to 32 Months

Sixty-nine (45%) patients had their dizziness disappear, and another 60 (39%) patients experienced reduced dizziness such that it represented no problem for them in daily living. Only eight (5%) patients found no change in dizziness, and 3 (2%) found their dizziness worse than before the change to the stepped-up dosing schedule. Remarkably, an 84% relief of dizziness was achieved with the stepped up dosing.

Hearing Loss after a Period of 3 to 31 Months

In sixty-four patients (51%) hearing improved, and in fifty-nine patients (47%) hearing was unchanged. In two patients (2%) hearing was worse than when they began the stepped-up dosing schedule. Untreated, these patients would have been expected to undergo further decline in their hearing.

Tinnitus or Ear Noise after 2 to 31 Months

Four patients (5%) experienced disappearance of their tinnitus, while 60 patients (71%) experienced a reduction of tinnitus to a point where it was no longer a problem for them. In eighteen patients (21%) it was the same as before the dose of 30 mg twice weekly, and in two patients (2%) it was worse. Significantly, a 76% improvement in tinnitus or ear noise was achieved.

Example 3

In a third study, the following populations having the symptom stated were treated with both risedronate (in a stepped up dosing schedule, i.e., at least 150% of the recommended dose for treating osteoporosis) and etidronate (in the recommended dose for treating osteoporosis).

| Symptom | Patient Total | Male | Female | Age Range | Mean Age |
| --- | --- | --- | --- | --- | --- |
| Meniere's syndrome | 6 | 3 | 3 | 32-82 | 52 |
| Dizziness | 15 | 7 | 8 | 26-83 | 50 |
| Hearing Loss | 13 | 6 | 7 | 37-91 | 65 |
| Tinnitus | 12 | 4 | 7 | 25-78 | 58 |

The dosing schedule depended on the individual and their condition to be treated. The schedules comprised two cycles of etidronate for two weeks followed by risedronate for four weeks; two cycles of etidronate for two weeks followed by risedronate for six weeks; and/or a maintenance schedule of etidronate for two weeks followed by risedronate for eleven weeks. All patients received calcium plus vitamin D, and calcium plus fluoride throughout the alternating treatment. The following results were obtained:

Meniere's Syndrome after a Period of 1 to 9 Months:

Three patients (50%) saw their dizziness disappear, while one patient (17%) experienced an improvement such that they were able to carry on a regular lifestyle free of disabling dizziness. In no instances was the dizziness the same or worse with the alternating dosing schedule.

One patient (17%) found their hearing to be better, while four patients (66%) found their hearing the same and only one (17%) found hearing to be worse than with the prior bisphosphonate treatment.

Ear noise did not disappear in any of the patients, but was better in one patient (17%) such that it was not a problem. In two patients (33%) ear noise was unchanged. In no patient was it worse that before beginning on the alternating dosing schedule. Clogging or fullness in the ear was not present at the time of the alternating schedule.

The results of this regimen are better than published surgical and other medical treatments for Meniere's syndrome.

Dizziness after 3 to 8 Months

Five patients (33%) had their dizziness disappear, and another eight (53%) experienced reduced dizziness such that it represented no problem for them in daily living. Only one patient (6%) found no change in the dizziness and one patient (6%) found their dizziness worse than before the change to the alternating dosing schedule. Remarkably, an 86% relief of dizziness was achieved with the alternating dosing schedule.

Hearing Loss after 3 to 7 Months

In four patients (31%) hearing improved, and in eight patients (62%) hearing did not change. In one patient (7%) hearing was worse than when they started the alternating dosing schedule. Untreated, these patients would have been expected to undergo further decline in their hearing.

Tinnitus or Ear Noise after 3 to 8 Months

Six patients (55%) experienced a reduction in tinnitus to a point where it was no longer a problem for them. In five patients (45%) it was the same as before alternating dosing schedule, and in no patients was it worse. Significantly, more than half of the patients experienced an improvement in tinnitus or ear noise, and in no patient did the condition worsen.

Example #4

Intravenous Administration

In a fourth study, the following populations having the symptom stated were administered a zolendronic acid injection in 4 mg per injection no more frequently than every three months. The frequency of administration was dependent upon the patient response and the impending indication. Some patients were also administered etidronate. All patients received calcium plus vitamin D and/or calcium plus fluoride throughout the treatment.

| Symptom | Patient Total | Male | Female | Age Range | Mean Age |
| --- | --- | --- | --- | --- | --- |
| Meniere's syndrome | 1 | 1 | 0 | 47 | 47 |
| Dizziness | 3 | 0 | 3 | 44-54 | 50 |
| Hearing Loss | 5 | 4 | 1 | 57-74 | 64 |
| Tinnitus | 1 | 1 | 0 | 52 | 52 |

The following results were obtained:

Meniere's Syndrome after Six Months

The patient experienced an improvement in dizziness such that he was able to carry on a regular lifestyle free of disabling dizziness.

In addition, his hearing was the same, and ear noise was the same. The results of this regimen show promising results for patients diagnosed with Meniere's syndrome.

Dizziness after 4 to 12 Months

Two of the patients had their dizziness disappear, and the third patient experienced reduced dizziness such that it represented no problem for them in daily living. Remarkably, almost 100% relief of dizziness was achieved.

Hearing Loss after 2 to 10 Months

In four patients (80%) hearing was unchanged. In one patient (20%) hearing was worse than when they began the zolendronic acid injections. Untreated, these patients would have been expected to undergo further decline in their hearing. Two of the patients were administered etidronate in the recommended dose for osteoporosis in addition to the zoledronic acid injections. In one patient hearing loss ceased and in the other patient, hearing loss was worse.

Tinnitus or Ear Noise after 10 Months

The patient was also administered etidronate in the recommended dose for osteoporosis in addition to the zoledronic acid injections. He experienced a reduction of tinnitus to a point where it was no longer a problem for him. Significantly, the injections plus etidronate resulted in improvement in tinnitus or ear noise.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, procedures, and the like are cited throughout this application, the disclosures of which are incorporated herein by reference in their entireties.

What is claimed is:

1. A method of treating otosclerosis in a human in need thereof which comprises administering to the human a bisphosphonate in an amount that is at least about 150% of a recommended dose for osteoporosis in said human.

2. The method of claim 1, wherein the method comprises administering to the human a bisphosphonate in an amount that is about 150% to 300% of the recommended dose for osteoporosis.

3. The method of claim 1, wherein the bisphosphonate is risedronate or a pharmaceutically acceptable salt thereof.

4. The method of claim 3, wherein the dose of risedronate is from about 45 mg to 105 mg per week.

5. The method of claim 1, wherein the administration is oral.

6. The method of claim 1, wherein the bisphosphonate is etidronate and the dose is at least 600 mg to 1200 mg of bisphosphonate per week for 1 to 3 weeks, every 6 to 13 weeks.

7. The method of claim 1, wherein the administration further comprises daily dosing of calcium, vitamin D, fluoride, or a combination thereof.

8. A method of treating otosclerosis in a human in need thereof which comprises alternating administration of a first and a second bisphosphonate.

9. The method of claim 8, wherein the first bisphosphonate is selected from the group consisting of etidronate, tiludronate, and pharmaceutically acceptable salts thereof.

10. The method of claim 8, wherein the second bisphosphonate is selected from the group consisting of risedronate, zolendronic acid, and pharmaceutically acceptable salts thereof.

11. The method of claim 8, wherein the administration further comprises daily dosing of calcium, vitamin D, fluoride, or a combination thereof.

12. The method of claim 8, wherein administration of the second bisphosphonate continues for about 1 to 52 weeks and is followed by administration of the first bisphosphonate for about 1 to 3 weeks, every 6 to 13 weeks.

13. The method of claim 8, wherein the dosage of the second bisphosphonate is at least about 150% of a recommended dose for osteoporosis in said human and the dosage of the first bisphosphonate is at least about 150% of a recommended dose for osteoporosis in said human.

14. The method of claim 8, wherein the dosage of the second bisphosphonate is at least about 150% of a recommended dose for osteoporosis in said human and the dosage of the first bisphosphonate is a recommended dose for osteoporosis in said human.

15. A method of treating otosclerosis in a human in need thereof, which method comprises administering a bisphosphonate intravenously.

16. The method of claim 15, wherein the dosage of the bisphosphonate is at least about 150% of a recommended dose for osteoporosis in said human.

17. The method of claim 15, wherein the bisphosphonate is zoledronic acid.

18. The method of claim 15, wherein the amount of the bisphosphonate is about 2 mg to 6 mg, administered about 2 to 10 times a year.

19. The method of claim 15, further comprising oral administration of a bisphosphonate wherein the bisphosphonate is selected from the group consisting of etidronate, risedronate, alendronate, and tiludronate.

20. A method of treating otosclerosis in a human in need thereof which comprises administering to the human ibandronate or a pharmaceutically acceptable salt thereof in an amount that is at least about 150% of a recommended dose for osteoporosis in said human.

21. The method of claim 20, wherein the dose of ibandronate or the pharmaceutically acceptable salt thereof is from about 3.75 mg to 7.5 mg per week.

* * * * *